US00PP11280P

United States Patent [19]

Strickland

[11] Patent Number: Plant 11,280

[45] Date of Patent: Mar. 14, 2000

[54] BLUE BEECH TREE NAMED 'CCSQU'

[75] Inventor: Thomas J. Strickland, Statesboro, Ga.

[73] Assignee: Tree Introductions, Inc., Bishop, Ga.

[21] Appl. No.: 09/016,832

[22] Filed: Jan. 30, 1998

[51] Int. Cl.[7] ..... A01H 5/00

[52] U.S. Cl. ..... Plt./216

[58] Field of Search ..... Plt./152, 216

[56] References Cited

U.S. PATENT DOCUMENTS

P.P. 10,676 11/1998 Beat ..... Plt./216

*Primary Examiner*—Howard J. Locker

*Assistant Examiner*—Wendy A. Baker

*Attorney, Agent, or Firm*—Klarquist Sparkman Campbell Leigh & Whinston LLP

[57] ABSTRACT

A blue beech tree named 'CCSQU' having an upright compact growth habit with a dense foliage canopy, with branches extending upwardly at steep angles and also capable of being reproduced reliably from vegetative cuttings or by budding.

7 Drawing Sheets

DESCRIPTION

The present invention relates to a new and distinct variety of *Carpinus caroliniana*, blue beech, which has been given the varietal name 'CCSQU'.

I discovered my new tree as a chance seedling growing in 1992 in a cultivated area at Shady Grove Nursery in Orangeburg, S.C., and purchased the tree in 1993 when it was transplated to its current location in a nursery location in Bulloch County, Ga. As I observed the original tree of my new variety, the uniqueness of this tree became apparent because of its more upright growing form.

I observed this original tree of my new variety for a period of time and believe it is particularly useful in landscape setting where upright tree forms are important, such as along streets, buildings and in planters.

In contrast, cultivated blue beech has in its entirety been represented by seedling material that is extremely variable in growth habit and usually develops a broader-rounded outline. The broader habit and lack of uniformity result in pruning and siting problems.

Blue beech is a small to medium size tree that matures between thirty and forty feet, is heat and drought tolerant, develops good fall color, and has a native range from Canada to Florida. There is a definite need for smaller trees that have these qualities and can be grown over a wide geographic area. Consequently, a new variety of blue beech which has a tighter and more upright growing habit and displays clonal consistency is particularly useful.

My new variety has been asexually propagated by budding and from softwood cuttings at my direction. Asexual propagation has been accomplished in Bullock County, Ga. by budding on *Carpinus caroliniana* seedling rootstock.

This propagation and observation of the resulting progeny have proven the characteristics of my new variety of blue beech to be firmly fixed. Furthermore, these observations have confirmed that my new variety represents a new and improved variety of blue beech as particularly evidenced by the unique combination of dense, upright growth habit, and uniform and clean abscission of leaves in the fall, and which can reliably be asexually propagated using vegetative propagation techniques.

The accompanying photographs depict the color of the tree and foliage of my new variety as nearly true as is reasonably possible to make the same in a color illustration of this character.

My 'CCSQU' variety of blue beech has not been observed under all growing conditions and thus variations may occur as a result of different growing conditions. The following is a detailed description of my new variety of blue beech with color terminology in accordance with The Royal Horticultural Society Colour Chart (R.H.S.) published by The Royal Horticultural Society of London. The observations are of trees growing in a nursery in Bulloch County, Ga.

My new variety of blue beech is characterized by its unique upright habit. In 1993, the initially discovered tree of my new variety was six years old and was transplanted to a nursery in Bulloch County, Ga. It is now five and three-fourths inches caliper twelve inches above the ground. In December of 1997, the tree was twenty feet high and ten feet wide. Its height to width ratio was 2.0. This alone distinguishes my new variety from typical *Carpinus caroliniana* trees. The national champion blue beech in Ulster County, N.Y., is sixty-nine feet high and fifty-six feed wide with a height to width ratio of 1.23. The height to width ratio of the champion is not unusual for the species and serves to emphasize the significantly unique upright growth habit of my new variety.

The growth rate observed in Bulloch County, Ga., is comparable to that of seedling trees. Progeny propagated from softwood cuttings of my new variety growing at this location have reached four feet in two years. Progeny of the original tree grown under nursery conditions at this location have been observed to be about a three-fourths of an inch caliper increase per year.

My new tree maintains strongly ascending branches forming a compact, upright oval outline. In contrast, other blue birch seedlings which I have observed do not exhibit this compact upright growth. The unique growth habit insures its capacity for use in areas where growing space is restricted, particularly along streets and buildings or sites which will not accommodate a spreading canopy.

Figure 1:
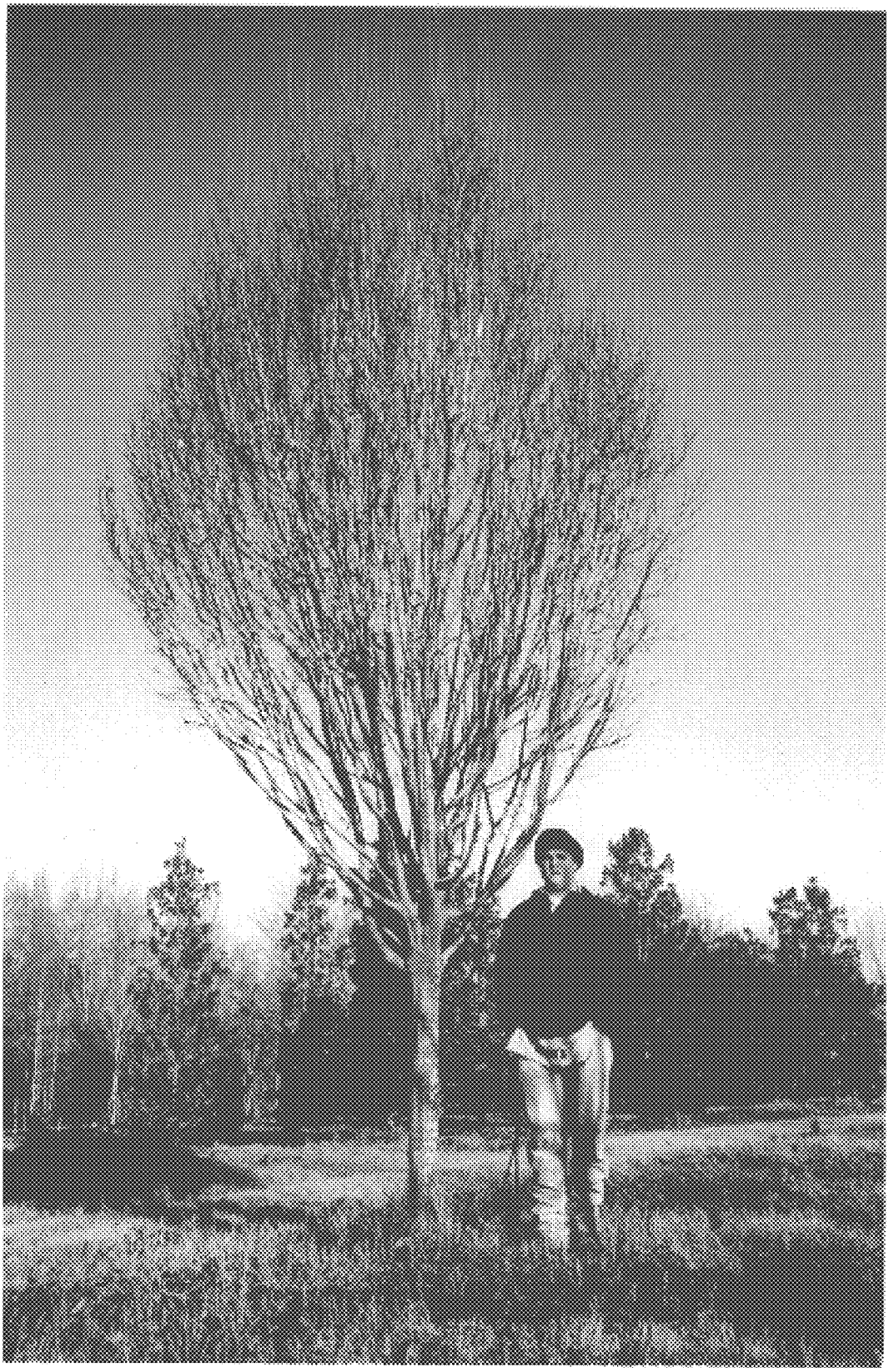
FIG. 1 is a photograph of an entire tree of my new variety.
Figure 2:
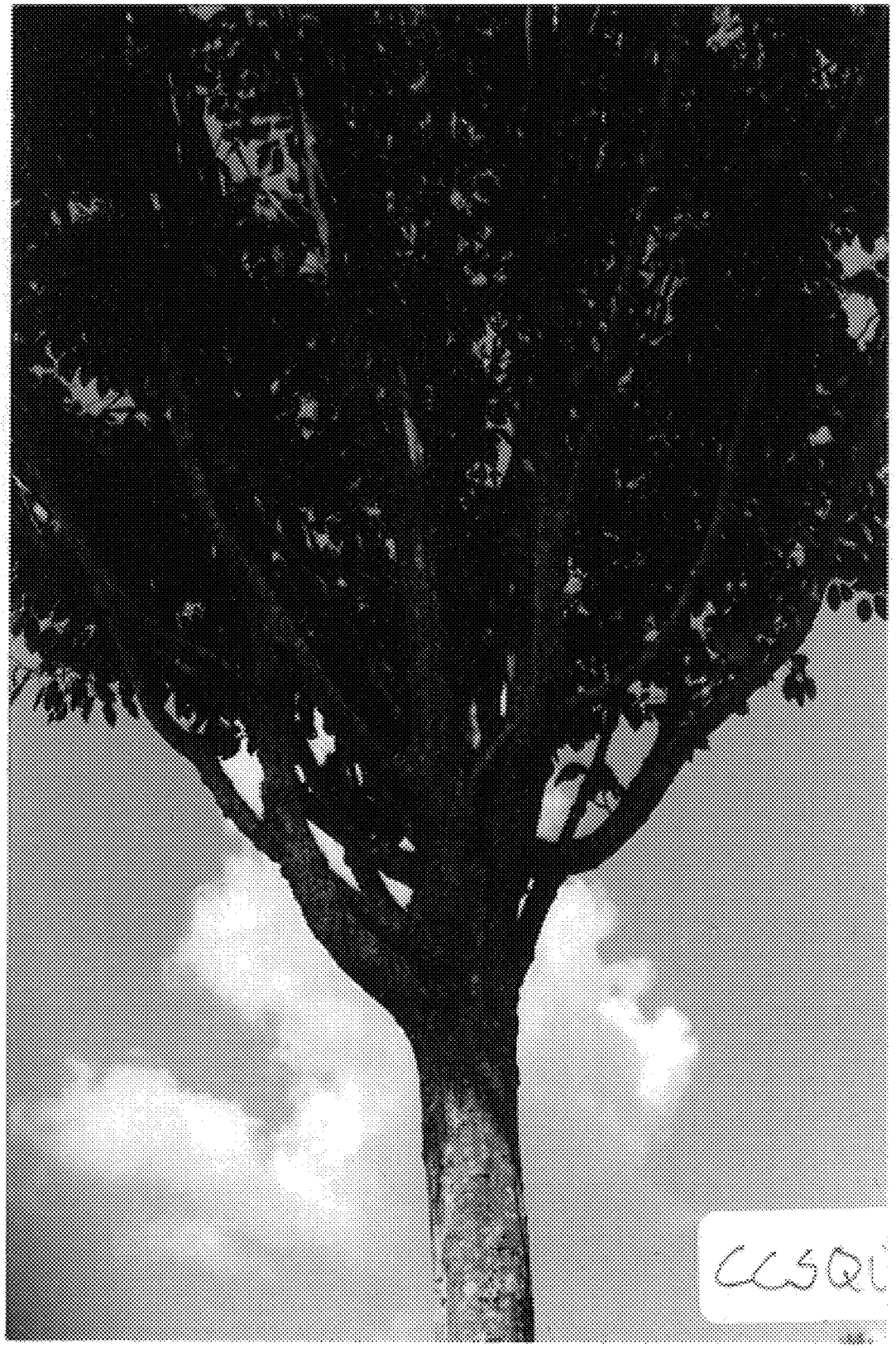
FIG. 2 is a close up of a portion of the branches of a tree of my new variety showing typical branch angles.
Figure 3:
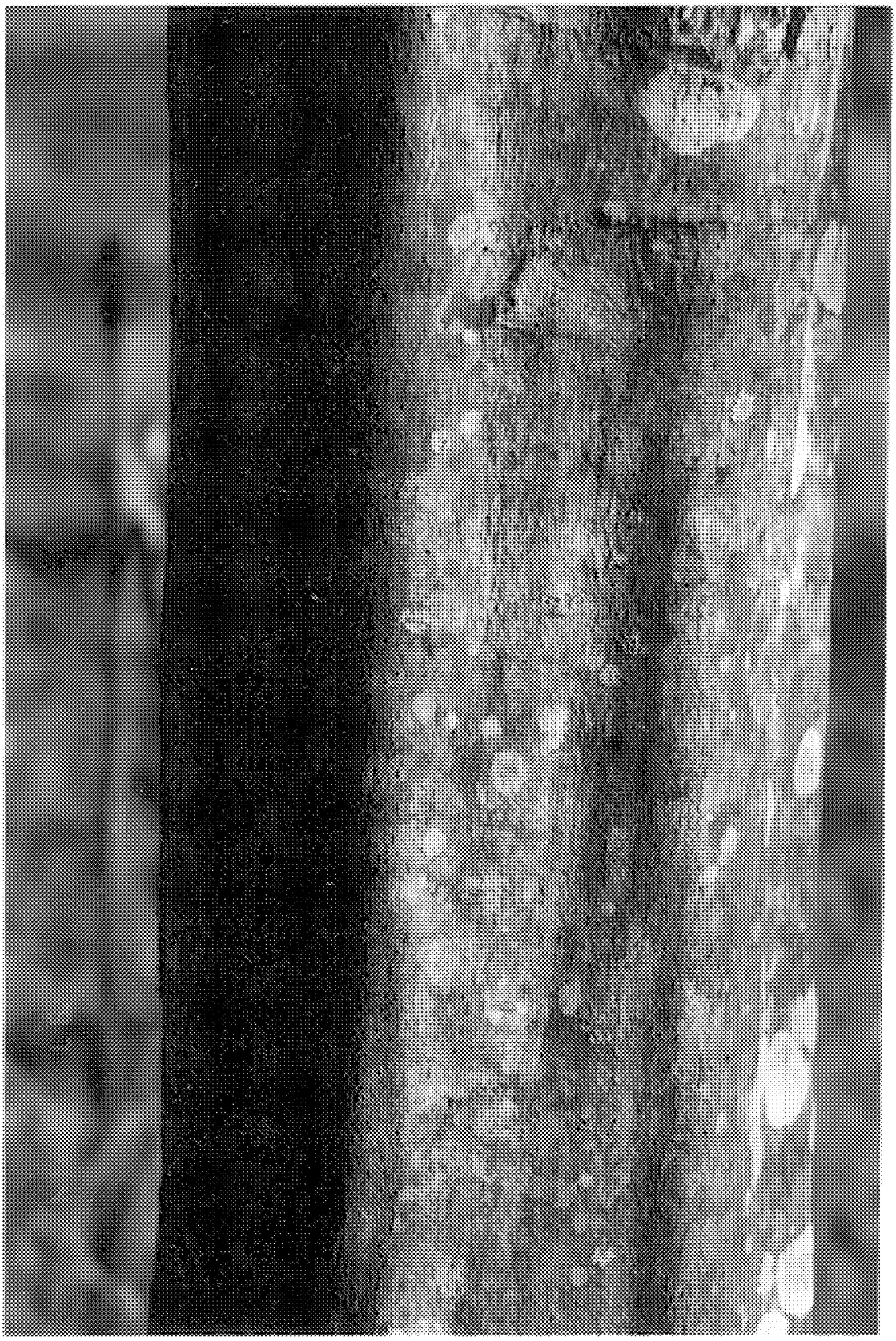
FIG. 3 is a close up of a trunk of my new variety showing mature bark.
Figure 4:
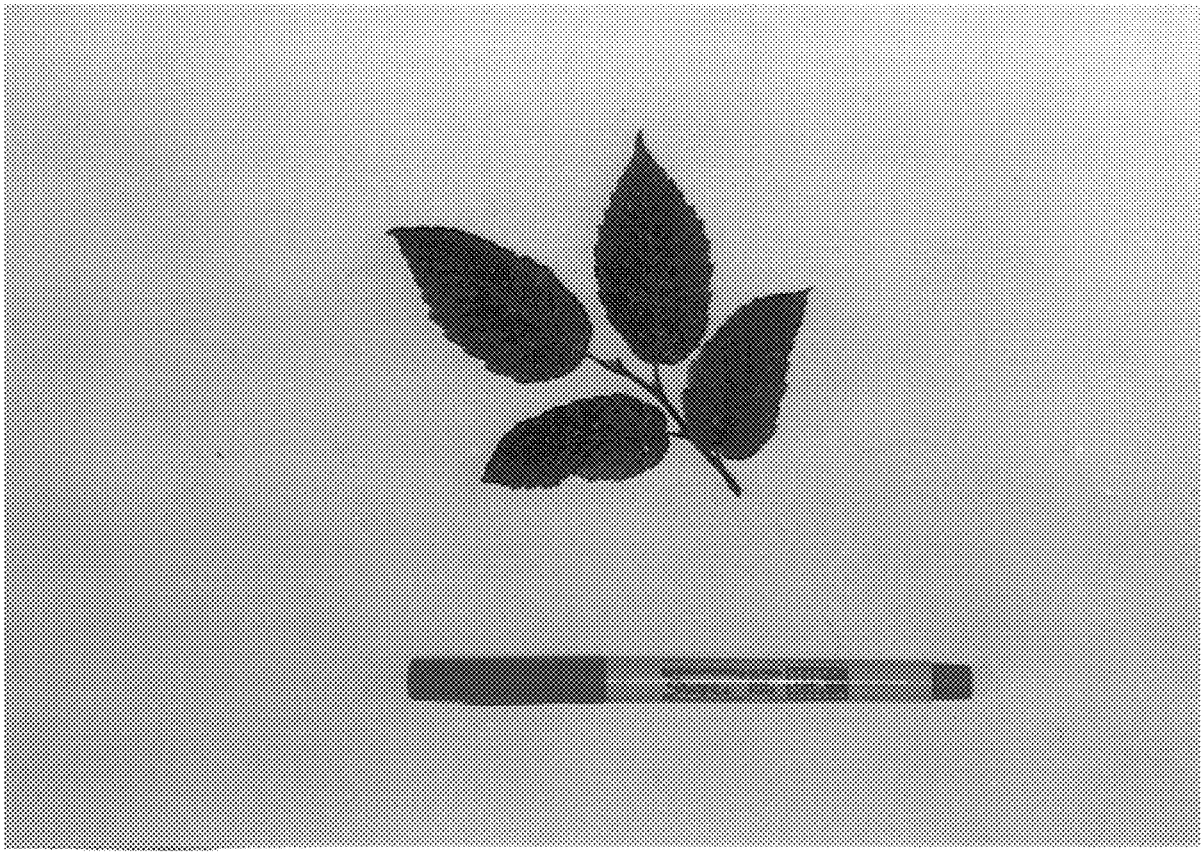
FIG. 4 is a close-up of the upper surface of several leaves from a tree of my new variety.
Figure 5:
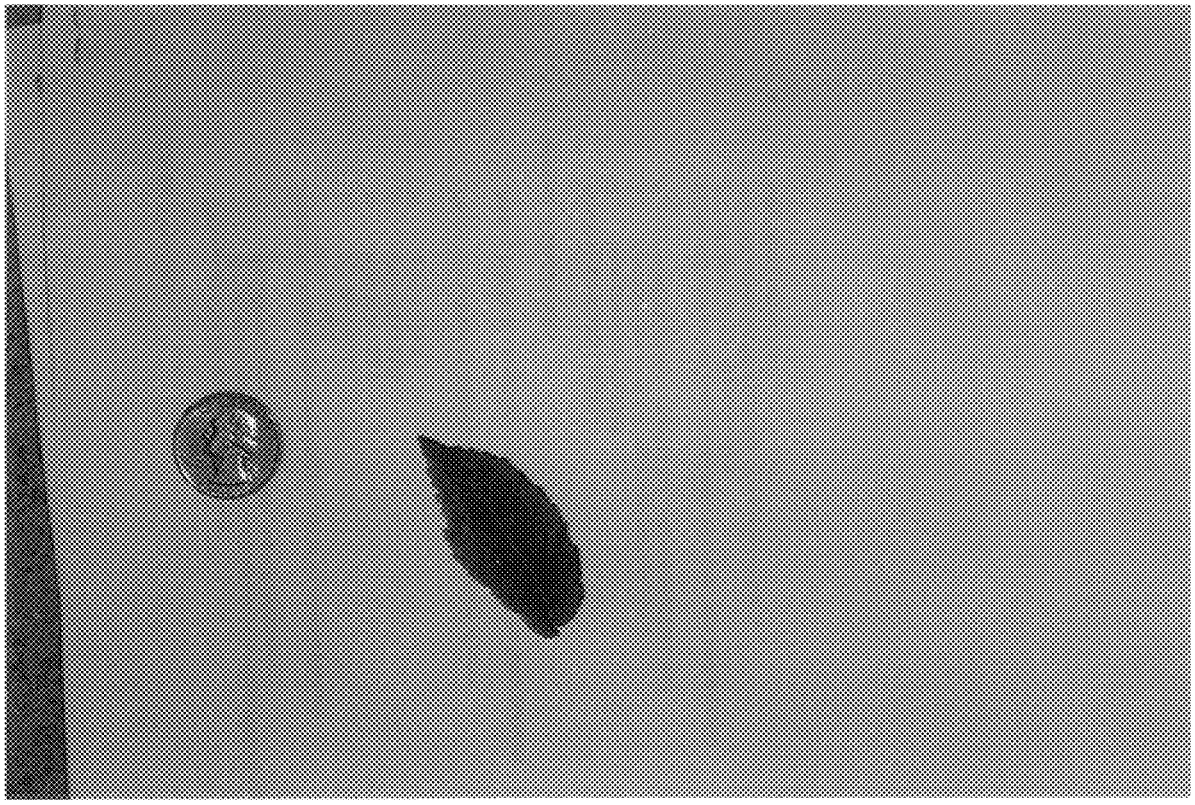
FIG. 5 is a close up of the upper surface of a single leaf from a tree of my new variety.
Figure 6:
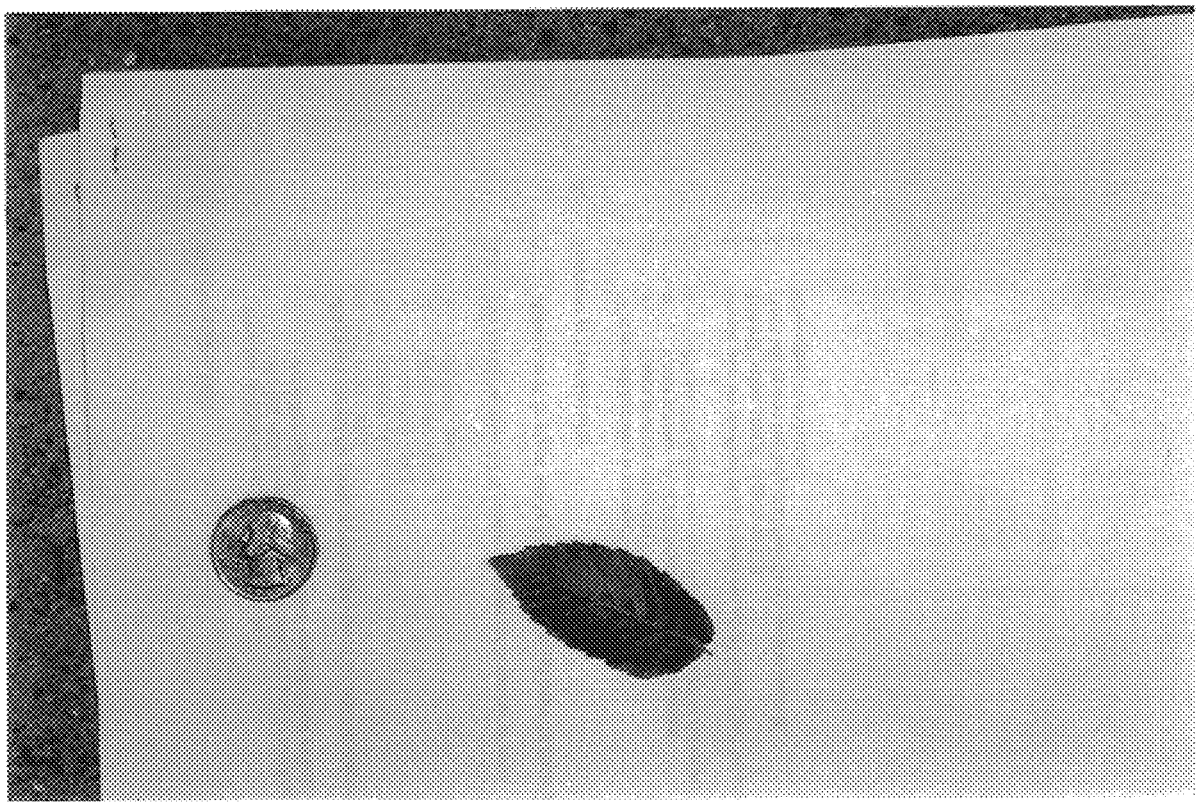
FIG. 6 is a close up of the lower surface of a single leaf from a tree of my new variety.
Figure 7:
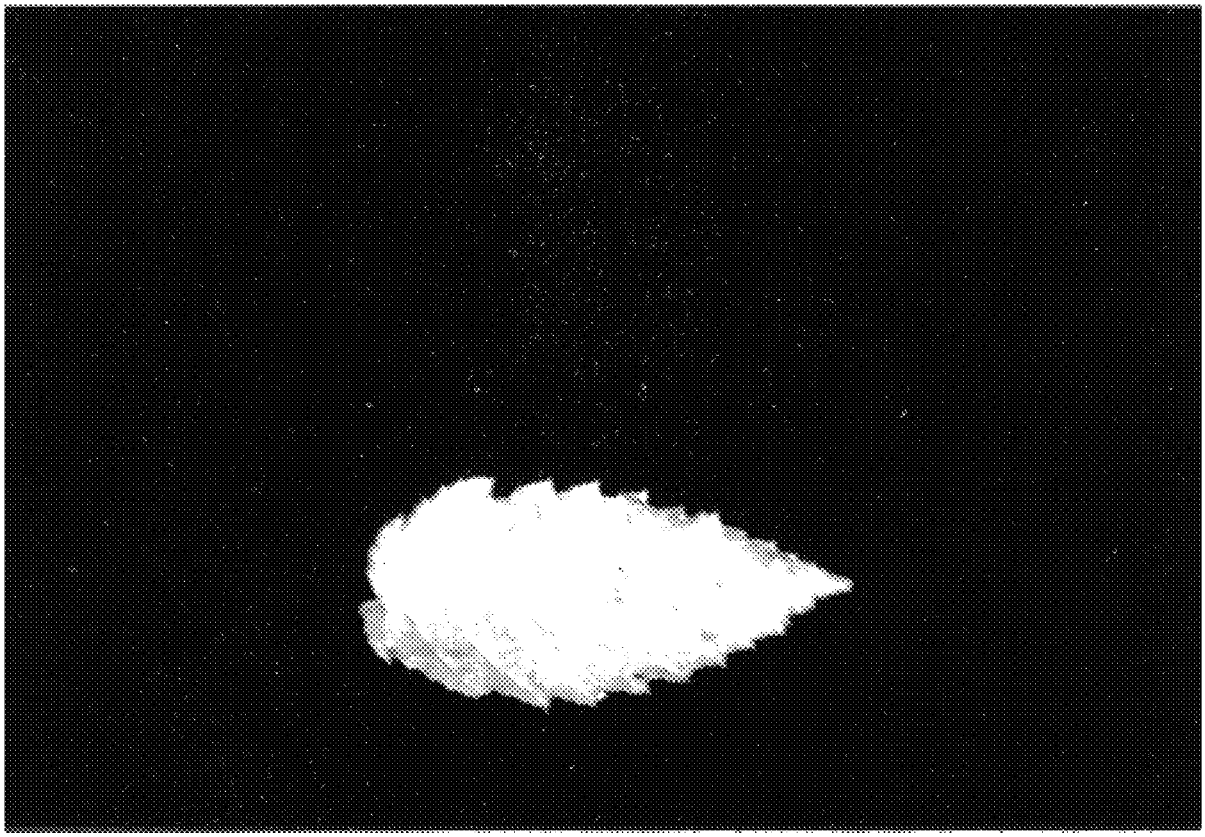
FIG. 7 is a close up of the upper surface of a leaf showing the fall color from a tree of my new variety.

More specifically, my new tree has a branching habit and dendritic pattern of an upright oval with branches that emerge at seventy degree angles with respect to the main leader and quickly ascend to essentially parallel the main leader, thus producing the compact, upright habit. As a result, as can be seen from FIG. 2, the tree of my new variety has a canopy characterized by close-knit branches and full dense foliage. In contrast, traditional seedling blue beeches are usually open and in youth must be pruned often to produce a compact habit.

The lower trunk and larger branches have the typical mature bark for the species, developing the smooth, sinewy gray (R.H.S. 201A) characteristics which provide aesthetic interest in the winter. First year stems are slightly more rigid than typical of the species. Stems average one-sixteenth to one-eighth inch diameter. The first year glabrous stems develop brown (R.H.S. 200A) coloration.

The leaves are similar to those of the species, simple with acuminate tips and ovate-oblong in shape with doubly serrate margins. Leaf arrangement is alternate. The upper leaf surface is dark yellow-green about (R.H.S. 147A). The lower surface is a flat yellow-green (R.H.S. 146B). In fall, the leaves turn a soft yellow-orange (R.H.S. 14C). The mature leaf averages two to three inches long, one to two inches wide, and petioles average one-fourth to one-half inch long. Mature leaves are glabrous except for pubescence on the veins below and with tufts of pubescence in vein axils.

The buds of the tree are typical of the species. Buds are imbricate, narrowly ovate to oblong with pointed tips, and range in size from one-sixth to one-fourth of an inch in length. Color varies from reddish brown to black. Pubescence may be present but is often absent; the bud scales often have downy edges and at times a tuft of down is present at the tip.

As observed in the original tree only, flowers and fruits are typical for the species, and the instant plant initiated flowers in its fifth growning season. The species is monoecious. Staminate catkins are one to one and one-half inches long, and the female flowers are two to four inches long and composed of three lobed bracts each one to one and one-half inches long. The middle lobe of each bract is usually the widest, up to one inch, and toothed. The fruit is a small, ribbed, seed-like nutlet surrounded by a veiny, three-lobed bract, usually about one inch long.

THE PLANT

Parentage: Chance blue beech seedling of unknown origin, growing in a cultivated area of the Shady Grove Nursery in Orangeburg, S.C.

Tree shape: Upright, densely branched, with uprightly ascending branches.

Trunk: Sturdy, upright, gray and sinewy with maturity.

Bark: Smooth and brown on young stems. The parent tree has been observed to develop the smooth, sinewy, gray bark that is typical of the species.

Mature bark color: (Observed in the original tree) Gray (R.H.S. 201A).

Branches: Sturdy, upright in orientation, emerging from the dominant leader at an angle of seventy degrees and then ascending upward to parallel the leader and form a strong crotch.

Leaves: Leaf shape is ovate-oblong and typical of the species.

Leaf surface: Upper leaf surface is dark yellow-green (R.H.S. 147A), glabrous, and slightly scabrous. The lower surface is a flat yellow-green (R.H.S. 146B) and glabrous except for pubescence on the veins below and with tufts of pubescence in vein axils.

Leaf size: Leaves average two to three inches long, one to two inches wide, with petioles one-fourth to one-half inch long.

Buds, flowers, and fruit: Observed in the original tree to be original of the species.

I claim:

1. A new and distinct variety of blue beech tree substantially as herein shown and described, characterized particularly as to novelty by its upright compact growth habit and dense foliage canopy.

* * * * *